(12) United States Patent
Horiki et al.

(10) Patent No.: US 9,337,379 B2
(45) Date of Patent: May 10, 2016

(54) METHOD FOR MANUFACTURING SOLAR CELL, AND SOLAR CELL

(71) Applicant: SEKISUI CHEMICAL CO., LTD., Osaka (JP)

(72) Inventors: Mayumi Horiki, Osaka (JP); Akinobu Hayakawa, Osaka (JP); Shunji Ohara, Osaka (JP); Taku Sasaki, Osaka (JP); Kazushi Ito, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/434,497

(22) PCT Filed: Nov. 22, 2013

(86) PCT No.: PCT/JP2013/081488
§ 371 (c)(1),
(2) Date: Apr. 9, 2015

(87) PCT Pub. No.: WO2014/084133
PCT Pub. Date: Jun. 5, 2014

(65) Prior Publication Data
US 2015/0263217 A1    Sep. 17, 2015

(30) Foreign Application Priority Data

Nov. 27, 2012 (JP) ................. 2012-258997
Mar. 26, 2013 (JP) ................. 2013-064759
Jun. 4, 2013 (JP) ................. 2013-118089

(51) Int. Cl.
| | |
|---|---|
| H01L 31/18 | (2006.01) |
| H01L 31/0224 | (2006.01) |
| H01L 51/42 | (2006.01) |
| C07D 265/02 | (2006.01) |
| C07C 249/08 | (2006.01) |
| H01L 51/44 | (2006.01) |
| H01L 31/0256 | (2006.01) |

(52) U.S. Cl.
CPC .......... *H01L 31/1884* (2013.01); *C07C 249/08* (2013.01); *C07D 265/02* (2013.01); *H01L 31/022425* (2013.01); *H01L 51/4213* (2013.01); *H01L 51/442* (2013.01); *H01L 2031/0344* (2013.01)

(58) Field of Classification Search
None
See application file for complete search history.

(56) References Cited

U.S. PATENT DOCUMENTS

2012/0006406 A1*  1/2012  Usui ................ H01G 9/2077
                                                       136/259

FOREIGN PATENT DOCUMENTS

| EP | 2 317 563 | 5/2011 |
|----|-----------|--------|
| JP | 2004-59358 | 2/2004 |
| JP | 2006-172722 | 6/2006 |
| JP | 4801899 | 6/2006 |
| JP | 2007-122932 | 5/2007 |
| JP | 2011-530783 | 12/2011 |
| JP | 2012-199228 | 10/2012 |

OTHER PUBLICATIONS

International Search Report issued Dec. 17, 2013 in International (PCT) Application No. PCT/JP2013/081488.

* cited by examiner

*Primary Examiner* — Seahvosh Nikmanesh
(74) *Attorney, Agent, or Firm* — Wenderoth, Lind & Ponack, L.L.P.

(57) ABSTRACT

The present invention aims to provide a method of producing a solar cell which can produce a porous inorganic oxide layer that has a high porosity and contains less impurities even by low-temperature firing. The present invention also aims to provide a solar cell produced by the method of producing a solar cell. The present invention directs to a method of producing a solar cell. The method includes: applying an inorganic oxide paste that contains inorganic oxide fine particles, a binder resin, and an organic solvent to a surface of a base to form an inorganic oxide layer on the base, the base including a conductive layer as an outermost layer thereof, the surface being a conductive layer-side surface; firing the inorganic oxide layer; irradiating the inorganic oxide layer with active energy rays or subjecting the inorganic oxide layer to ozonolysis to form a porous inorganic oxide layer; and laminating a semiconductor on the porous inorganic oxide layer.

9 Claims, No Drawings

METHOD FOR MANUFACTURING SOLAR CELL, AND SOLAR CELL

TECHNICAL FIELD

The present invention relates to a method of producing a solar cell. The method can produce a porous inorganic oxide layer that has a high porosity and contains less impurities even if low-temperature firing is employed. The present invention also relates to a solar cell produced by the method of producing a solar cell.

BACKGROUND ART

With issues of fossil fuel depletion or global warming as a backdrop, a great attention has recently been given to solar cells as a clean energy source. Research and development on them are being actively conducted. Silicon-based solar cells, typified by monocrystalline Si, polycrystalline Si, or amorphous Si solar cells, have been in practical use, but they are expensive, and shortage of the material Si has surfaced. In such a situation, demand for next-generation solar cells has been growing.

In response to the demand, organic solar cells such as dye-sensitized solar cells, organic thin film solar cells, and organic-inorganic hybrid solar cells have received attention in recent years.

A dye-sensitized solar cell typically includes as an electrode material a layer of titanium oxide formed on a base that includes a conductive layer (electrode). This titanium oxide layer serves to 1) adsorb sensitizing dye, 2) accept electrons injected from excited sensitizing dye, 3) transport electrons to the conductive layer, 4) offer a reaction site for electron transfer (reduction) from an iodide ion to dye, and 5) scatter and confine light. This layer is one of the most important factors to determine performances of the solar cell. When the titanium oxide layer serves to "1) adsorb sensitizing dye," the titanium oxide layer is required to absorb much sensitizing dye to improve photoelectric conversion efficiency. Accordingly, the titanium oxide layer is required to be porous, to have as large a surface area as possible, and to contain as little impurities as possible.

The titanium oxide layer as an electrode material is also used in organic thin film solar cells and organic-inorganic hybrid solar cells. In organic thin film solar cells and organic-inorganic hybrid solar cells, the titanium oxide layer is overlaid with a semiconductor, in which electrons and holes are generated by light excitation. To improve photoelectric conversion efficiency, the titanium oxide layer is required to have a larger contact area with the semiconductor, and therefore is required to be porous as in dye-sensitized solar cells.

Such a porous titanium oxide layer is generally formed by applying a paste containing titanium oxide particles and an organic binder on a base, volatilizing the solvent, and then removing the organic binder by high-temperature firing. This produces a porous layer in which the titanium oxide particles are sintered together and which has many fine voids in the layer. However, high-temperature firing at temperatures higher than 500° C. rules out the use of resin bases, which are increasingly needed these days for further reduction in costs. Low-temperature firing disadvantageously allows residues of the organic binder to be left on the surface of the titanium oxide particles, thus significantly reducing photoelectric conversion efficiency.

To overcome these problems, Patent Literature 1, for example, discloses a firing treatment at a low temperature using a paste which contains a reduced amount of an organic binder. The paste of Patent Literature 1, however, has a low viscosity, and thus makes it difficult to retain the shape of the applied paste. This paste therefore causes non-uniform film thickness and loss of shape of the film end, and when printed in a pattern of micro wiring, it causes coalescence of the wiring.

CITATION LIST

Patent Literature

Patent Literature 1: Japanese Patent No. 4801899

SUMMARY OF INVENTION

Technical Problem

An object of the present invention is to provide a method of producing a solar cell which can produce a porous inorganic oxide layer that has a high porosity and contains less impurities even if low-temperature firing is employed. Another object of the present invention is to provide a solar cell produced by the method of producing a solar cell.

Solution to Problem

The present invention directs to a method of producing a solar cell. The method includes: applying an inorganic oxide paste that contains inorganic oxide fine particles, a binder resin, and an organic solvent to a surface of a base to form an inorganic oxide layer on the base, the base including a conductive layer as an outermost layer thereof, the surface being a conductive layer-side surface; firing the inorganic oxide layer; irradiating the inorganic oxide layer with active energy rays or subjecting the inorganic oxide layer to ozonolysis to form a porous inorganic oxide layer; and laminating a semiconductor on the porous inorganic oxide layer.

The present invention is described in detail below.

As a result of keen examination, the present inventors have found that in a solar cell production method using an inorganic oxide paste containing inorganic oxide fine particles, a binder resin, and an organic solvent, irradiating an inorganic oxide layer with active energy rays or subjecting the layer to ozonolysis after firing enables production of a porous inorganic oxide layer that has a high porosity and contains less impurities even if the firing is performed at low temperatures, thus leading to a high photoelectric conversion efficiency. The inventors also have found that such a porous inorganic oxide layer allows sufficient adsorption or lamination of sensitizing dye or a semiconductor in a short period of time.

The inventors further found that adsorption or lamination of a semiconductor which is used in organic thin film solar cells or organic-inorganic hybrid solar cells on such a porous inorganic oxide layer results in an especially high photoelectric conversion efficiency, although adsorption of sensitizing dye also gives a high photoelectric conversion efficiency. Such findings have led to the completion of the present invention. The reason of this is unclear, but presumably that the adsorption degree of a semiconductor is less dependent on the state of the surface of the porous inorganic oxide layer than that of sensitizing dye.

The method of producing a solar cell of the present invention includes applying an inorganic oxide paste that contains inorganic oxide fine particles, a binder resin, and an organic solvent to a surface of a base to form an inorganic oxide layer on the base. The base includes a conductive layer as an outermost layer thereof. The surface is a conductive layer-side surface.

The inorganic oxide paste is applied to a surface of a base that includes a conductive layer as an outermost layer thereof to form an inorganic oxide layer. The surface is a conductive layer-side surface. Another layer (e.g., another inorganic oxide layer which does not become porous after fired) may optionally be present between the conductive layer and the inorganic oxide layer.

The lower limit of the thickness of the inorganic oxide layer formed by applying the inorganic oxide paste is preferably 100 nm, whereas the upper limit thereof is preferably 5000 nm. The lower limit is more preferably 150 nm, and the upper limit is more preferably 2000 nm.

The inorganic oxide paste may be applied by any method, and preferably by a spin coat method. Preferable application methods also include printing methods such as a screen printing method. If the base is flexible, a roll-to-roll continuous printing is very advantageous in terms of mass productivity and production cost. The application is preferably followed by drying.

The aperture size of the screen printing plate, the attack angle of the squeegee, the squeegee speed, and the squeegee pressure in the process by a screen printing method are preferably appropriately selected.

The base may be any base that includes a conductive layer as an outermost layer thereof. Examples thereof include a base including a transparent conductive layer formed on a transparent substrate. The transparent substrate may be any substrate which is transparent, and examples thereof include glass substrates such as silicate glass substrates. The glass substrate may be chemically or thermally tempered. Various plastic substrates may be used if they ensure light permeability.

The transparent substrate preferably has a thickness of 0.1 to 10 mm, and more preferably 0.3 to 5 mm.

Examples of the transparent conductive layer include layers made of conductive metal oxides such as $In_2O_3$ and $SnO_2$, and layers made of conductive materials such as metals. Examples of the conductive metal oxide include $In_2O_3$:Sn (ITO), $SnO_2$:Sb, $SnO_2$:F, ZnO:Al, ZnO:F, and $CdSnO_4$.

The inorganic oxide paste contains inorganic oxide fine particles. Examples of the inorganic oxide fine particles include titanium oxide fine particles, aluminum oxide fine particles, and silicon oxide fine particles, with titanium oxide fine particles being preferred. Titanium oxide is suitable because it has a broad bandgap, and it is a relatively abundant resource.

Examples of titanium oxide fine particles include fine particles of generally used rutile titanium oxide, anatase titanium oxide, and brookite titanium oxide, and fine particles of titanium oxide obtained by modifying these crystalline titanium oxides.

The lower limit of the average particle size of the inorganic oxide fine particles is preferably 5 nm, whereas the upper limit thereof is preferably 100 nm. The lower limit is more preferably 10 nm. The upper limit is more preferably 50 nm, and still more preferably 25 nm. If the average particle size is within the range, the resulting porous inorganic oxide layer can have a sufficient specific surface area. In addition, recombination of an electron and a hole can be prevented. Two or more fine particles having different particle size distributions may be used in combination.

The average particle size may be determined by observing fine particles with a transmission electron microscope (TEM) at a magnification proper to observe about 100 fine particles in one visual field, measuring the longest diameters of freely-selected 50 fine particles with a micrometer caliper, and calculating the average of the longest diameters.

The lower limit of the amount of the inorganic oxide fine particles is preferably 1% by weight in the inorganic oxide paste, whereas the upper limit thereof is preferably 75% by weight. If the amount of the inorganic oxide fine particles is 1% by weight or more, the resulting porous inorganic oxide layer can have a sufficient thickness. If the amount of the inorganic oxide fine particles is 75% by weight or less, an increase in the viscosity of the inorganic oxide paste can be suppressed, thus allowing smoother application. The lower limit of the amount of the inorganic oxide fine particles is more preferably 3% by weight. The upper limit thereof is more preferably 50% by weight, and still more preferably 35% by weight.

The inorganic oxide paste contains a binder resin. Examples of the binder resin include ethylcellulose (EC), (meth)acrylic resins, polyvinyl alcohol (PVA), polyvinyl butyral (PVB), polyethylene glycol, polystyrene, and polylactic acid. Among these, (meth)acrylic resin is preferred. The term "(meth)acrylic resins" herein means acrylic resins or methacrylic resins.

The inorganic oxide paste with a (meth)acrylic resin, which is excellent in low-temperature decomposition properties, will give less organic residues even if fired at low temperatures. Further, the (meth)acrylic resin is characterized by a low viscosity, and thus can markedly suppress change in viscometric properties of the inorganic oxide paste even if the solvent in the paste is volatilized due to work environment (e.g., long exposure to outside air, exposure to external forces such as strong shear force from devices such as a screen printing plate or a squeegee during screen printing). This enables stable application.

The (meth)acrylic resin may be any (meth)acrylic resin that is decomposed at low temperatures around 300° C. Suitable examples thereof include a polymer derived from at least one selected from the group consisting of methyl (meth)acrylate, ethyl (meth)acrylate, propyl(meth)acrylate, n-butyl (meth)acrylate, tert-butyl (meth)acrylate, isobutyl (meth)acrylate, cyclohexyl(meth)acrylate, 2-ethylhexyl(meth)acrylate, isobornyl(meth)acrylate, n-stearyl(meth)acrylate, benzyl (meth)acrylate, and (meth)acrylic monomers having a polyoxyalkylene structure. Here, the (meth)acrylate, for example, means an acrylate or a methacrylate. Among these, a polyisobutyl methacrylate (isobutyl methacrylate polymer), which is a polymer of isobutyl methacrylate and has a high glass transition temperature (Tg) and excellent low-temperature degreasing properties, is suitable because it allows the resulting paste to have a high viscosity with less resin.

The lower limit of the weight average molecular weight of the binder resin in terms of polystyrene is preferably 5000, whereas the upper limit thereof is preferably 500000. If the weight average molecular weight is 5000 or greater, the resulting inorganic oxide paste can exhibit a sufficient viscosity and can be suitably applied. If the weight average molecular weight is 500000 or smaller, stringing due to an increase in adhesion of the inorganic oxide paste can be prevented, and thus application properties are further improved. The upper limit of the weight average molecular weight is more preferably 100000, and still more preferably 50000. The weight average molecular weight in terms of polystyrene may be determined by GPC using, for example, column LF-804 (from SHOKO Co., Ltd.).

The amount of the binder resin in the inorganic oxide paste is not limited to particular values. The lower limit thereof is preferably 1% by weight, whereas the upper limit thereof is preferably 50% by weight. If the amount of the binder resin is 1% by weight or more, the inorganic oxide paste can have a sufficient viscosity, thus have improved application properties. If the amount of the binder resin is 50% by weight or less, the resulting inorganic oxide paste can have an appropriate viscosity and adhesion, thus have improved application properties.

The amount of the binder resin is preferably smaller than the amount of the inorganic oxide fine particles. If the amount of the binder resin is larger than that of the inorganic oxide fine particles, an increased amount of organic residues may remain after firing.

The inorganic oxide paste contains an organic solvent. The organic solvent is preferably one in which the binder resin is highly soluble and which has a high polarity. Examples of such an organic solvent include terpene solvents such as α-terpineol and γ-terpineol, alcohol solvents such as ethanol and isopropyl alcohol, polyalcohol solvents such as diol and triol, mixed solvents of the alcohol solvents/hydrocarbons, and heterocompounds such as dimethylformamide, dimethylsulfoxide, and tetrahydrofuran. Among these, terpene solvents are preferred.

The organic solvent preferably has a boiling point of 50 to 300° C. If the organic solvent has a boiling point of 50° C. or higher, the resulting inorganic oxide paste can be appropriately dried, and thus used in long-time continuous printing. If the organic solvent has a boiling point of 300° C. or lower, the resulting inorganic oxide paste can have improved drying properties in a drying step that is performed after application of the paste. The "boiling point" herein means the boiling point at normal pressure.

The lower limit of the amount of the organic solvent is preferably 55% by weight, whereas the upper limit thereof is preferably 95% by weight. If the amount of the organic solvent is within the above range, the resulting inorganic oxide paste can have an appropriate viscosity, thus have improved application properties. The lower limit is more preferably 60% by weight.

The inorganic oxide paste preferably contains a photo-acid-generating agent. If the paste contains a photo-acid-generating agent, organic substances can be decomposed by two kinds of decompositions, that is, decomposition by acid from the photo-acid-generating agent and oxidation decomposition due to the below-mentioned treatment after firing. As a result, residues can be effectively decomposed.

The photo-acid-generating agent may be any photo-acid-generating agent that produces acid when irradiated with light. Examples thereof include compounds containing an acid compound that is ester-linked to a light-absorbing compound. Specific examples of the photo-acid-generating agent include: sulfonium salt compounds such as those available under the trade names of "TPS-105" (CAS No. 66003-78-9), "TPS-109" (CAS No. 144317-44-2), "MDS-105" (CAS No. 116808-67-4), "MDS-205" (CAS No. 81416-37-7), "DTS-105" (CAS No. 111281-12-0), "NDS-105" (CAS No. 195057-83-1), and "NDS-165" (CAS No. 316821-98-4) from Midori Kagaku Co., Ltd.; iodonium salts compounds such as those available under the trade names of "DPI-105" (CAS No. 66003-76-7), "DPI-106" (CAS No. 214534-44-8), "DPI-109" (CAS No. 194999-82-1), "DPI-201" (CAS No. 6293-66-9), "BI-105" (CAS No. 154557-16-1), "MPI-105" (CAS No. 115298-63-0), "MPI-106" (CAS No. 260061-46-9), "MPI-109" (CAS No. 260061-47-0), "BBI-105" (CAS No. 84563-54-2), "BBI-106" (CAS No. 185195-30-6), "BBI-109" (CAS No. 194999-85-4), "BBI-110" (CAS No. 213740-80-8), and "BBI-201" (CAS No. 142342-33-4) from Midori Kagaku Co., Ltd.; sulfonic acid ester compounds such as those available under the trade names of "NAI-106" (naphthalimide camphorsulfonic acid salt, CAS No. 83697-56-7), "NAI-100 (CAS No. 83697-53-4), "NAI-1002" (CAS No. 76656-48-9), "NAI-1004" (CAS No. 83697-60-3), "NAI-101" (CAS No. 5551-72-4), "NAI-105" (CAS No. 85342-62-7), "NAI-109" (CAS No. 171417-91-7), "NI-101" (CAS No. 131526-99-3), "NI-105" (CAS No. 85342-63-8), "NDI-101" (CAS No. 141714-82-1), "NDI-105" (CAS No. 133710-62-0), "NDI-106" (CAS No. 210218-57-8), "NDI-109" (CAS No. 307531-76-6), "PAI-01" (CAS No. 17512-88-8), "PAI-101" (CAS No. 82424-53-1), "PAI-106" (CAS No. 202419-88-3), "PAI-1001" (CAS No. 193222-02-5), "SI-101" (CAS No. 55048-39-0), "SI-105" (CAS No. 34684-40-7), "SI-106" (CAS No. 179419-32-0), "SI-109" (CAS No. 252937-66-9), "PI-105" (CAS No. 41580-58-9), and "PI-106" (CAS No. 83697-51-2) from Midori Kagaku Co., Ltd., "PAG-121," "CGI1397," "CGI1325," "CGI1380," "CGI1311," "CGI263," and "CGI268" from Chiba Specialty Chemicals Corp.; and compounds having $BF_4^-$ as a counter ion such as those available under the trade names of "DTS200" (CAS No. 203573-06-2) from Midori Kagaku Co., Ltd., and "RHODORSIL PHOTOINITIATOR-2074" (CAS No. 178233-72-2) from Rhodia Japan Ltd. These photo-acid-generating agents may be used singly, or in combination of two or more thereof. Among these, photo-acid-generating agents that have the structure represented by Formula (1) are preferred.

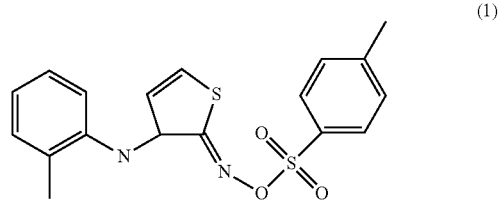 [SMILES: Cc1ccc(S(=O)(=O)O/N=C2\SC=CC2Nc2ccccc2C)cc1]

(1)

The amount of the photo-acid-generating agent is not limited to particular values. The lower limit thereof is preferably 0.0025% by weight, whereas the upper limit thereof is preferably 2.5% by weight. If the amount of the photo-acid-generating agent is 0.0025% by weight or more, addition of the photo-acid-generating agent can give sufficient effects for decomposing organic substances. If the amount of the photo-acid-generating agent is 2.5% by weight or less, for example, an increase in the proportion of the light absorbing compound is suppressed, and adverse effects of the increase can be reduced accordingly. The lower limit of the amount of the photo-acid-generating agent is more preferably 0.025% by weight, whereas the upper limit thereof is more preferably 1.25% by weight.

Preferably, the inorganic oxide paste contains the binder resin and the organic solvent in a total amount of 1% by weight or less after the paste is heated from 25° C. to 300° C. in air atmosphere at a temperature-increasing rate of 10° C./min.

In this case, the inorganic oxide paste after heating has less impurities on the surface. This allows easy binding (necking) between the inorganic oxide fine particles, resulting in reduction in resistance between the particles. This leads to a high photoelectric conversion efficiency.

If the total amount is more than 1% by weight, impurities remain on the surface of the inorganic oxide fine particles. This may prevent favorable lamination of the semiconductor. The total amount herein is an amount relative to the inorganic oxide fine particles.

The inorganic oxide paste not only has excellent application properties, but also can suitably give a porous inorganic oxide layer that has a high porosity and contains less impurities even if low-temperature firing is employed.

Additionally, the inorganic oxide paste is excellent in compatibility with organic solvents generally used in washing screen printing plates, and therefore can be sufficiently washed and removed after use. This prevents clogging of screen printing plates, and enables stable screen printing for a long period of time.

The inorganic oxide paste may be produced by, for example, a method including a step for mixing the inorganic oxide fine particles, the binder resin, and the organic solvent. The way of the mixing may be, for example, mixing using a two-roll mill, a tree-roll mill, a bead mill, a ball mill, a disperser, a planetary mixer, a planetary centrifugal mixer, a kneader, an extruder, a mix rotor, a stirrer, or the like.

The method of producing a solar cell of the present invention includes firing the inorganic oxide layer.

The conditions for the firing, such as the temperature, the time, and the atmosphere can be appropriately adjusted depending on such factors as the kind of the base on which the paste is applied. For example, the firing is preferably performed under air atmosphere or an inert gas atmosphere at a temperature in a range of about 50 to 800° C. for 10 seconds to 12 hours. With the method of producing a solar cell of the present invention, which can produce a porous inorganic oxide layer that has a high porosity and contains less impurities even if low-temperature firing is employed, a relatively low firing temperature of 300° C. or lower may be employed.

The drying and the firing may be performed at a time at a single temperature or two or more times at different temperatures.

The method of producing a solar cell of the present invention includes irradiating the inorganic oxide layer with active energy rays or subjecting the layer to ozonolysis to form a porous inorganic oxide layer.

The step allows oxidation decomposition of organic residues present in a minute amount in the inorganic oxide layer due to a catalytic activity effect of the inorganic oxide. This contributes to further improvement of properties of the solar cell. This effect is noticeable especially when a (meth)acrylic resin is used as the binder resin. In addition, when inorganic oxide fine particles having a small average particle size are used, contact area between the inorganic oxide and the binder resin can be increased, which can further increase the catalytic activity effect of the inorganic oxide.

The step of irradiating the inorganic oxide layer with active energy rays or subjecting the layer to ozonolysis to form a porous inorganic oxide layer may be performed simultaneously with the step of firing the inorganic oxide layer, or may be performed after the firing step.

Examples of the active energy rays include ultraviolet rays, plasma, and electron rays.

If the active energy rays are ultraviolet rays, the inorganic oxide layer is preferably irradiated with ultraviolet rays such that the accumulated light amount of ultraviolet rays is 100 J/cm$^2$ or larger. If the accumulated light amount is 100 J/cm$^2$ or larger, organic residues can be sufficiently removed. The lower limit of the accumulated light amount is more preferably 150 J/cm$^2$, whereas the upper limit thereof is preferably 10000 J/cm$^2$. The accumulated light amount may be determined by simplified calculation according to "irradiation intensity (mW/cm$^2$)×irradiation time (seconds)."

The irradiation intensity of ultraviolet rays is preferably 0.5 to 1000 mW/cm$^2$.

The irradiation time of ultraviolet rays is preferably 1 second to 300 minutes, and more preferably 1 second to 60 minutes. If the irradiation intensity is too small or if the irradiation time is too short, the removal of organic residues only partially proceeds, making the effects of the irradiation insufficient. If the irradiation intensity is too large or the irradiation time is too long, the transparent substrate may be degraded by ultraviolet rays or thermally degraded.

If the active energy rays are plasma, the plasma treatment intensity is preferably 50 to 1000 W.

The plasma treatment time is preferably 1 second to 30 minutes, and more preferably 10 seconds to 10 minutes. If the treatment intensity is too small or if the treatment time is too short, the removal of organic residues only partially proceeds, making the effect of the treatment insufficient. If the treatment intensity is too large or the treatment time is too long, the substrate may be degraded by plasma or thermally degraded.

The atmosphere during the plasma treatment may be, for example, nitrogen, oxygen, or argon atmosphere. If a nitrogen plasma treatment is performed, a partial nitriding treatment can be performed. In addition, such a nitrogen plasma treatment can repair oxygen defects of an oxygen plasma-treated inorganic oxide.

The way of irradiating the active energy rays is not limited to particular ways. Examples thereof include irradiation with ultraviolet rays using a low-pressure mercury lamp, a high-pressure mercury lamp, or a mercury-xenon lamp and irradiation with plasma using a plasma generator.

In irradiation with the active energy rays, the inorganic oxide layer is preferably irradiated with the active energy rays from both the front side (side opposite the substrate) and the back side (substrate side) of the inorganic oxide layer. This allows the inside of the inorganic oxide layer to be sufficiently irradiated with the active energy rays. As a result, the effects of irradiation with the active energy rays can be sufficiently produced even if the accumulated light amount is small, contributing to reduction in the time of the whole production process. The irradiation from the front side and the back side may be performed simultaneously, or sequentially in several steps.

In the method of producing a solar cell of the present invention, it is preferred that a step of further irradiating the inorganic oxide layer with pulsed white light having a small pulse width is performed after the step of irradiating the inorganic oxide layer with active energy rays or subjecting the layer to ozonolysis to produce a porous inorganic oxide layer. Irradiation with pulsed white light fuses the surfaces of the inorganic fine particles in the porous inorganic oxide layer together, and thus densifies the particles. This can reduce the surface resistance.

The pulsed light preferably has a pulse width of 0.1 to 10 ms. Pulsed light with such a pulse width enables instantaneous irradiation with an intense light energy.

The accumulated light amount of the pulsed light is not limited to particular values, but preferably 4 J/cm$^2$ or larger. In this case, energy that is sufficient for fusion of the inorganic oxide fine particles is applied. The accumulated light amount is preferably 15 to 40 J/cm$^2$. The number of irradiations is preferably 1 to 5.

The pulsed light irradiation may be carried out with, for example, a halogen flash lamp, a xenon flash lamp, or a LED flash lamp. A xenon flash lamp is preferred.

The method of producing a solar cell of the present invention includes laminating a semiconductor on the porous inorganic oxide layer.

The porous inorganic oxide layer enables sufficient lamination of a semiconductor thereon in a short period of time. The laminate thus obtained, in which at least the porous inorganic oxide layer and the semiconductor are formed on the base including the conductive layer as an outermost layer, may be further optionally overlaid with another layer. Thereafter, an opposite electrode (conductive layer) is disposed on the resulting laminate, whereby a solar cell can be produced. The solar cell thus obtained can achieve a high photoelectric conversion efficiency. Although adsorption of sensitizing dye on the porous inorganic oxide layer gives a high photoelectric conversion efficiency, adsorption or lamination of a semiconductor which is used in organic thin film solar cells or organic-inorganic hybrid solar cells gives an especially high photoelectric conversion efficiency.

The semiconductor may be any semiconductor which contains a semiconductor serving as an N-type semiconductor and a semiconductor serving as a P-type semiconductor. Such a semiconductor is generally used in organic thin film solar cells or organic-inorganic hybrid solar cells. In such a semiconductor, electrons and holes are generated by light excitation. The electrons move through the N-type semiconductor, and the holes move through the P-type semiconductor, whereby an electric field is generated.

Specific examples of preferred semiconductor include sulfides of elements of group XV of the periodic table and organic-inorganic hybrid semiconductors.

Preferred examples of the sulfide of an element of group XV of the periodic table include antimony sulfide and bismuth sulfide. For improvement of photoelectric conversion efficiency, antimony sulfide is more preferred. These sulfides of elements of group XV of the periodic table may be used singly, or in combination of two or more thereof. The sulfide of an element of group XV of the periodic table may be a complex sulfide which contains two or more elements of group XV of the periodic table in one molecule.

The organic-inorganic hybrid semiconductor may be any semiconductor that contains both an organic component and an inorganic component in the structure. Preferably, it contains a halogen. Such an organic-inorganic hybrid semiconductor with a halogen in the structure is soluble in organic solvents, and thus applicable in inexpensive printing methods.

The organic-inorganic hybrid semiconductor is preferably represented by the formula R-M-$X_3$ (R is an organic molecule, M is a metal atom, X is a halogen atom). In this case, the organic-inorganic hybrid semiconductor preferably has a cubic structure in which a metal atom M occupies the body center position, organic molecules R occupy cube corner positions, and halogen atoms X occupy face center positions.

The R is an organic molecule, and preferably a molecule represented by $C_lN_mH_n$ (l, m, and n each are positive integers). Specific examples thereof include methylamine, ethylamine, propylamine, butylamine, pentylamine, hexylamine, dimethylamine, diethylamine, dipropylamine, dibutylamine, dipentylamine, dihexylamine, trimethylamine, triethylamine, tripropylamine, tributylamine, tripentylamine, trihexylamine, ethylmethylamine, methylpropylamine, butylmethylamine, methylpentylamine, hexylmethylamine, ethylpropylamine, ethylbutylamine, imidazole, azole, pyrrole, aziridine, azirine, azetidine, azete, azole, imidazoline, carbazole, ions thereof, and phenethyl ammonium. Among these, methylamine, ethylamine, propylamine, butylamine, pentylamine, hexylamine, ions thereof, and phenethyl ammonium are preferred. Methylamine, ethylamine, propylamine, and ions thereof are more preferred.

The M is a metal atom. Examples thereof include lead, tin, zinc, titanium, antimony, bismuth, nickel, iron, cobalt, silver, copper, gallium, germanium, magnesium, calcium, indium, aluminum, manganese, chromium, molybdenum, and europium. These atoms M may be used singly, or in combination of two or more thereof.

The X is a halogen atom. Examples thereof include chlorine, bromine, and iodine. These atoms X may be used singly, or in combination of two or more thereof. The X preferably includes iodine for a narrow energy bandgap.

The semiconductor may be laminated by, for example, preparing a solution for forming a semiconductor film containing the semiconductor or a precursor thereof dissolved therein, applying the solution by a spin coat method, and drying it.

The method of forming a solar cell of the present invention can produce a porous inorganic oxide layer that has a high porosity and contains less impurities even if low-temperature firing is employed, thus leading to a high photoelectric conversion efficiency. A solar cell produced by the method of producing a solar cell of the present invention is one aspect of the present invention.

Advantageous Effects of Invention

The present invention provides a method of producing a solar cell which can produce a porous inorganic oxide layer that has a high porosity and contains less impurities even if low-temperature firing is employed. The present invention also provides a solar cell produced by the method of producing a solar cell.

DESCRIPTION OF EMBODIMENTS

The present invention is described in more detail below with reference to, but not limited to, examples.

Example 1

Preparation of Titanium Oxide Paste

Titanium oxide fine particles (mixture of particles having an average particle size of 10 nm with those having an average particle size of 30 nm), polyisobutyl methacrylate (weight average molecular weight: 50000) as a binder resin, a mixed solvent of α-terpineol (boiling point: 219° C.) and ethanol (boiling point: 78° C.) as an organic solvent were uniformly mixed with a bead mill so that the composition shown in Table 1 was achieved. Thus, a titanium oxide paste was prepared.
(Formation of Porous Titanium Oxide Layer)

A FTO transparent electrode (thickness: 1000 nm) as a negative electrode was formed on a glass substrate. The substrate with the electrode was ultrasonically washed with pure water, acetone, and methanol for 10 minutes each in the stated order, and then dried.

A solution of titanium isopropoxide in ethanol (2% by weight) was applied to the surface of the FTO transparent electrode by a spin coat method to form an electron-transport buffer layer, and the buffer layer was fired at 150° C. for 10 minutes (titanium oxide layer (1)). The titanium oxide paste prepared above was applied by a spin coat method to the glass substrate surface where the FTO transparent electrode and the titanium oxide layer (1) were formed, and fired at 150° C. for 10 minutes (titanium oxide layer (2)). The titanium oxide layers (1) and (2) had a total thickness of about 500 nm. Thereafter, the titanium oxide layer (2) was irradiated with ultraviolet rays from the side opposite the glass substrate, that is, from the front side, with a high-pressure mercury lamp (HLR100T-2 from SEN LIGHTS Corp.) at an irradiation intensity of 500 mW/cm$^2$ for 60 minutes. Thus, a porous titanium oxide layer was obtained.
(Preparation of Solar Cell)

Antimony chloride and thiourea (molar ratio: 1:2) were dissolved in N,N-dimethylformamide (DMF) so that the total concentration of the antimony chloride and the thiourea was adjusted to 20% by weight. Thus, a solution (1) for forming a semiconductor film was obtained. The solution (1) for forming a semiconductor film was applied to the porous titanium oxide layer obtained above by a spin coat method, and dried. Separately, Spiro-OMeTAD (68 mM), tert-butyl pyridine (55 mM), and lithium bis(trifluoromethylsulfonyl)imide salt (9 mM) were dissolved in chlorobenzene (25 μL) to prepare a solution (2) for forming a semiconductor film. The solution (2) for forming a semiconductor film was applied to the obtained semiconductor layer by a spin coat method, and dried.

A gold film (thickness of 100 nm) as a positive electrode was formed on the prepared semiconductor layer by vacuum deposition. Thus, a solar cell was obtained.

Examples 2 to 14, Comparative Example 1

Porous titanium oxide layers and solar cells were obtained in the same manner as in Example 1 except that the binder resin, the inorganic oxide fine particles, conditions for firing, conditions for treatment (ultraviolet ray irradiation or plasma irradiation) after the firing, and the semiconductor were changed as shown in Table 1.

In Example 12, the semiconductor layer of $CH_3NH_3PbI_2Cl$ was formed from a solution (1) for forming a semiconductor film prepared by dissolving $CH_3NH_3I$ and $PbCl_2$ (molar ratio 3:1) in N,N-dimethylformamide (DMF). In Examples 13 and 14, a plasma treatment was performed under the conditions shown in Table 1 instead of ultraviolet ray irradiation.

<Evaluation 1>

The solar cells obtained in Examples 1 to 14 and Comparative Example 1 were evaluated in the following manner. The results are shown in Table 1.

(Evaluation of Performance of Solar Cell)

A power source (Model 236, produced by Keithley Instruments Inc.) was connected between the electrodes of the each of the obtained solar cells. The photoelectric conversion efficiency of the solar cells was determined with a solar simulator (from Yamashita Denso Corp.) at an intensity of 100 mW/cm$^2$.

Table 1 also shows the relative conversion efficiency of the solar cells when the photoelectric conversion efficiency of a solar cell that was produced under the same conditions except that firing was performed at 550° C. for 60 minutes is taken as 1.

Comparative Example 2

Preparation of Titanium Oxide Paste

Titanium oxide fine particles (average particle size: 20 nm), polyisobutyl methacrylate (weight average molecular weight: 50000) as a binder resin, and α-terpineol (boiling point: 219° C.) as an organic solvent were uniformly mixed with a bead mill so that the composition shown in Table 1 was achieved. Thus, a titanium oxide paste was prepared.

(Formation of Titanium Oxide Layer)

The obtained titanium oxide paste was printed in the shape of a 5 mm square on a glass substrate having a 25-mm square FTO transparent electrode thereon, and fired at 150° C. for 60 minutes. The printing conditions were minutely controlled such that the resulting porous titanium oxide layer had a thickness of 10 μm.

(Preparation of Dye-Sensitized Solar Cell)

The substrate with the porous titanium oxide layer thereon was immersed in a solution of Ru complex dye (N719) in acetonitrile:t-butanol=1:1 (concentration: 0.3 mM) for a day. Thus, the sensitizing dye was adsorbed on the surface of the porous titanium oxide layer.

Thereafter, a film (thickness: 30 μm) of HIMILAN was placed on the substrate such that the film surrounded the entire porous titanium oxide layer except one side of the titanium oxide layer. A glass substrate with a platinum electrode deposited thereon was placed on the film. Then, a solution of lithium iodide and iodine in acetonitrile was poured into the opening between the titanium oxide layer and the substrate with a platinum electrode deposited thereon. And the part not surrounded by the film was sealed. Thus, a dye-sensitized solar cell was obtained.

Comparative Examples 3 and 4

Porous titanium oxide layers and dye-sensitized solar cells were obtained in the same manner as in Comparative Example 2 except that the treatment (ultraviolet irradiation) after firing was performed as shown in Table 1.

<Evaluation 2>

The dye-sensitized solar cells obtained in Comparative Examples 2 to 4 were evaluated in the following manner. The results are shown in Table 1.

(Evaluation of Properties of Dye-Sensitized Solar Cell)

A power source (Model 236, produced by Keithley Instruments Inc.) was connected between the electrodes of the each of the obtained dye-sensitized solar cells. The photoelectric conversion efficiency of the solar cells was determined with a solar simulator (produced by Yamashita Denso Corporation) at an intensity of 100 mW/cm$^2$.

Table 1 shows the relative conversion efficiency of the solar cells when the photoelectric conversion efficiency of a dye-sensitized solar cell that was produced under the same conditions except that firing was performed at 550° C. for 60 minutes is taken as 1.

TABLE 1

| | Paste composition ratio (% by weight) | | | | | | | | | | | |
|---|---|---|---|---|---|---|---|---|---|---|---|---|
| | Binder resin | | | Titanium oxide fine particles | | | | | | Aluminum oxide fine particles Average particle | Organic solvent | |
| | Polyisobutyl methacrylate | EC | PVB | Average particle size (nm) | | | | | | size (nm) | α-terpineol | Ethanol |
| | | | | 10 | 10 and 30 | 50 | 90 | 120 | 150 | 15 | | |
| Example 1 | 4 | — | — | — | 8 | — | — | — | — | — | 22 | 66 |
| Example 2 | — | 4 | — | — | 8 | — | — | — | — | — | 22 | 66 |
| Example 3 | — | — | 4 | — | 8 | — | — | — | — | — | 22 | 66 |
| Example 4 | 4 | — | — | — | 8 | — | — | — | — | — | 22 | 66 |
| Example 5 | 4 | — | — | — | 8 | — | — | — | — | — | 22 | 66 |
| Example 6 | 4 | — | — | — | — | 8 | — | — | — | — | 22 | 66 |
| Example 7 | 4 | — | — | — | — | — | 8 | — | — | — | 22 | 66 |
| Example 8 | 4 | — | — | — | — | — | — | 8 | — | — | 22 | 66 |
| Example 9 | 4 | — | — | — | — | — | — | — | 8 | — | 22 | 66 |
| Example 10 | 4 | — | — | 8 | — | — | — | — | — | — | 22 | 66 |
| Example 11 | 4 | — | — | — | — | — | — | — | — | 8 | 22 | 66 |
| Example 12 | 4 | — | — | — | 8 | — | — | — | — | — | 22 | 66 |
| Example 13 | 4 | — | — | — | 8 | — | — | — | — | — | 22 | 66 |

TABLE 1-continued

| | | | | | | | | | | | | | |
|---|---|---|---|---|---|---|---|---|---|---|---|---|---|
| Example 14 | 4 | — | — | — | 8 | — | — | — | — | — | — | 22 | 66 |
| Comparative Example 1 | 4 | — | — | — | 8 | — | — | — | — | — | — | 22 | 66 |
| Comparative Example 2 | 10 | — | — | — | 25 | — | — | — | — | — | — | 22 | — |
| Comparative Example 3 | 10 | — | — | — | 25 | — | — | — | — | — | — | 22 | — |
| Comparative Example 4 | 10 | — | — | — | 25 | — | — | — | — | — | — | 22 | — |

| | Firing | | Ultraviolet ray irradiation | | | Plasma irradiation | | | | Photoelectric conversion efficiency | |
|---|---|---|---|---|---|---|---|---|---|---|---|
| | Temperature (°C.) | Time (min) | Irradiation intensity (mW/cm$^2$) | Ultraviolet ray irradiation time (min) | Accumulated light amount (J/cm$^2$) | Treatment intensity (W) | Treatment time (min) | Treatment atmosphere | Semiconductor | Measured value (%) | Relative conversion efficiency (%) |
| Example 1 | 150 | 10 | 500 | 60 | 1800 | — | — | — | Antimony sulfide | 3.0 | 90.9 |
| Example 2 | 150 | 10 | 500 | 60 | 1800 | — | — | — | | 2.4 | 77.4 |
| Example 3 | 150 | 10 | 500 | 60 | 1800 | — | — | — | | 1.8 | 75.0 |
| Example 4 | 150 | 10 | 200 | 10 | 120 | — | — | — | | 2.3 | 69.7 |
| Example 5 | 150 | 10 | 200 | 7 | 84 | — | — | — | | 1.9 | 57.6 |
| Example 6 | 150 | 10 | 500 | 60 | 1800 | — | — | — | | 2.5 | 83.3 |
| Example 7 | 150 | 10 | 500 | 60 | 1800 | — | — | — | | 2.1 | 84.0 |
| Example 8 | 150 | 10 | 500 | 60 | 1800 | — | — | — | | 1.7 | 77.3 |
| Example 9 | 150 | 10 | 500 | 60 | 1800 | — | — | — | | 1.5 | 83.3 |
| Example 10 | 150 | 10 | 500 | 60 | 1800 | — | — | — | | 2.8 | 87.5 |
| Example 11 | 150 | 10 | 500 | 60 | 1800 | — | — | — | | 0.5 | 55.6 |
| Example 12 | 150 | 10 | 500 | 60 | 1800 | — | — | — | CH$_3$NH$_3$PbI$_2$Cl | 8.3 | 80.6 |
| Example 13 | 150 | 10 | — | — | — | 400 | 10 | Ar | Antimony sulfide | 3.1 | 93.93 |
| Example 14 | 150 | 10 | — | — | — | 400 | 10 | N$_2$ | Antimony sulfide | 3.2 | 96.96 |
| Comparative Example 1 | 150 | 10 | — | — | — | — | — | — | Antimony sulfide | 0.1 | — |
| Comparative Example 2 | 150 | 60 | — | — | — | — | — | — | Ru complex dye (N719) | 1.43 × 10$^{-3}$ | 0.015 |
| Comparative Example 3 | 150 | 60 | 100 | 30 | 180 | — | — | — | | 4.1 | 43.5 |
| Comparative Example 4 | 150 | 60 | 100 | 60 | 360 | — | — | — | | 4.4 | 47.2 |

Comparison between the photoelectric conversion efficiency of the solar cells obtained in Examples 1 to 14 and that of the solar cell obtained in Comparative Example 1 shows that the treatment (ultraviolet ray irradiation or plasma irradiation) after firing results in a high photoelectric conversion efficiency.

Comparison between the photoelectric conversion efficiency of the solar cells obtained in Examples 1 to 14 and that of the dye-sensitized solar cells obtained in Comparative Examples 3 and 4 shows that solar cells (Examples 1 to 14) produced through adsorption or lamination of a semiconductor which is used in organic thin film solar cells or organic-inorganic hybrid solar cells on the porous titanium oxide layer gives an especially high photoelectric conversion efficiency as compared with the dye-sensitized solar cells (Comparative Examples 3 and 4) produced through adsorption of sensitized dye on the porous titanium oxide layer.

INDUSTRIAL APPLICABILITY

The present invention provides a method of producing a solar cell which can produce a porous inorganic oxide layer that has a high porosity and contains less impurities even if low-temperature firing is employed. The present invention also provides a solar cell produced by the method of producing a solar cell.

The invention claimed is:

1. A method of producing a solar cell, the method comprising:
    applying an inorganic oxide paste that contains inorganic oxide fine particles, a binder resin, and an organic solvent to a surface of a base to form an inorganic oxide layer on the base,
    the base including a conductive layer as an outermost layer thereof,
    the surface being a conductive layer-side surface;
    firing the inorganic oxide layer;
    irradiating the inorganic oxide layer with active energy rays to form a porous inorganic oxide layer, or subjecting the inorganic oxide layer to ozonolysis to form a porous inorganic oxide layer; and
    laminating a semiconductor on the porous inorganic oxide layer.

2. The method according to claim 1,
    wherein the binder resin is a (meth)acrylic resin.

3. The method according to claim 2,
    wherein the (meth)acrylic resin is polyisobutyl methacrylate.

4. The method according to claim 1,
    wherein the organic solvent has a boiling point within the range of 50 to 300° C.

5. The method according to claim 1,
    wherein the inorganic oxide fine particles comprise titanium oxide fine particles.

6. The method according to claim 1,
wherein the semiconductor is a sulfide of an element of group XV of the periodic table or an organic-inorganic hybrid semiconductor.

7. The method according to claim 1,
wherein the porous inorganic oxide layer is formed by irradiating the inorganic oxide layer with active energy rays, such that the accumulated light amount is 100 J/cm$^2$ or larger, and
wherein the active energy rays are ultraviolet rays.

8. The method according to claim 1,
wherein the inorganic oxide fine particles have an average particle size of 5 to 100 nm.

9. A solar cell produced by the method according to claim 1.

* * * * *